(12) United States Patent
Black et al.

(10) Patent No.: US 9,827,027 B2
(45) Date of Patent: Nov. 28, 2017

(54) ORTHOPEDIC ANCHOR ASSEMBLY

(71) Applicant: GLOBUS MEDICAL, INC., Audubon, PA (US)

(72) Inventors: Michael Black, Phoenixville, PA (US); Jon Suh, Ambler, PA (US); Christopher Angelucci, Schwenksville, PA (US); Matthew Hansell, Schwenksville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/148,594

(22) Filed: May 6, 2016

(65) Prior Publication Data
US 2016/0249962 A1    Sep. 1, 2016

Related U.S. Application Data

(63) Continuation of application No. 13/273,625, filed on Oct. 14, 2011, now Pat. No. 9,358,050.

(51) Int. Cl.
| | | |
|---|---|---|
| *A61B 17/80* | (2006.01) | |
| *A61B 17/92* | (2006.01) | |
| *A61B 17/88* | (2006.01) | |
| *A61B 17/86* | (2006.01) | |

(52) U.S. Cl.
CPC ...... *A61B 17/8038* (2013.01); *A61B 17/8033* (2013.01); *A61B 17/8605* (2013.01); *A61B 17/8872* (2013.01); *A61B 17/92* (2013.01); *A61B 2017/922* (2013.01)

(58) Field of Classification Search
CPC ........ A61N 17/80; A61N 17/88; A61N 17/92; A61N 17/8038; A61N 17/8872
USPC .................. 606/280–299, 300–331
See application file for complete search history.

(56) References Cited

U.S. PATENT DOCUMENTS

| | | | |
|---|---|---|---|
| 5,169,400 A | 12/1992 | Muhling et al. | |
| 5,527,339 A * | 6/1996 | Koscher | A61B 17/29 606/205 |
| 6,554,834 B1 | 4/2003 | Crozet et al. | |
| 8,361,126 B2 * | 1/2013 | Perrow | A61B 17/8047 606/287 |
| 2006/0122604 A1 | 6/2006 | Gorhan et al. | |
| 2006/0167456 A1 | 7/2006 | Johnston et al. | |
| 2006/0264936 A1 | 11/2006 | Partin et al. | |
| 2007/0288025 A1 * | 12/2007 | Peukert | A61B 17/8038 606/86 A |
| 2010/0256686 A1 | 10/2010 | Fisher et al. | |
| 2011/0172719 A1 | 7/2011 | Gorhan et al. | |
| 2011/0251649 A1 | 10/2011 | Puekert et al. | |

* cited by examiner

*Primary Examiner* — Christopher Beccia

(57) ABSTRACT

An orthopedic assembly is described that comprises an orthopedic device, an anchor, and a locking mechanism. The orthopedic device can be a plate member having an aperture that is configured to receive the anchor. The anchor can include a head, neck and shank portion. The head portion can include a plurality of arms separated by grooves that are capable of splaying. The assembly is configured such that when the locking mechanism is inserted into the head portion, this causes expansion of the arms of the head. This expansion locks and secures the anchor to the orthopedic device. Various instruments are provided that can deliver the locking mechanism to the anchor, and can provide impact to lock functionality.

18 Claims, 12 Drawing Sheets

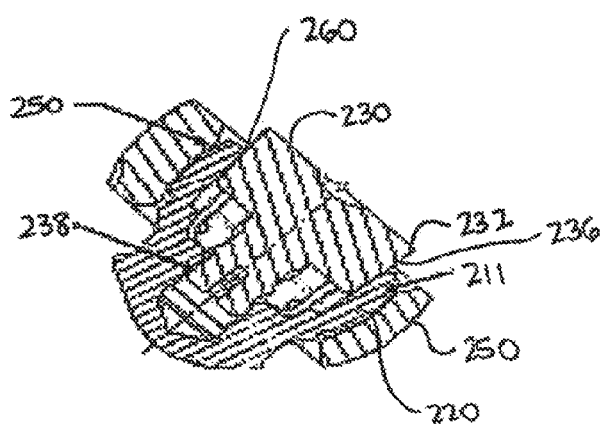
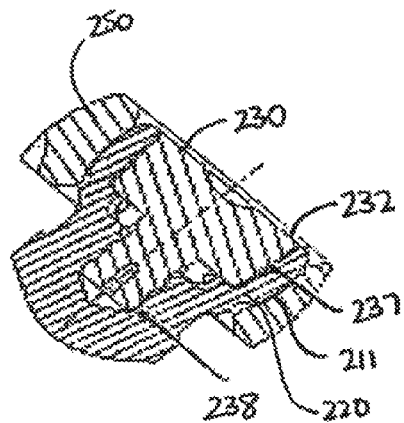
FIG. 8A  FIG. 8B
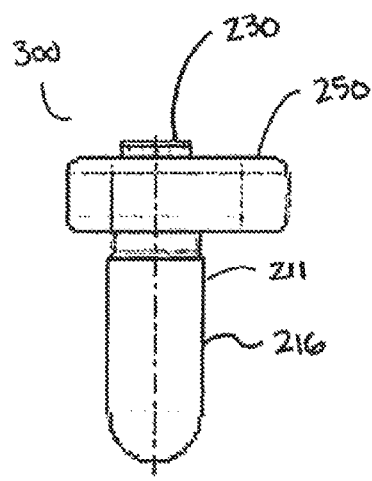
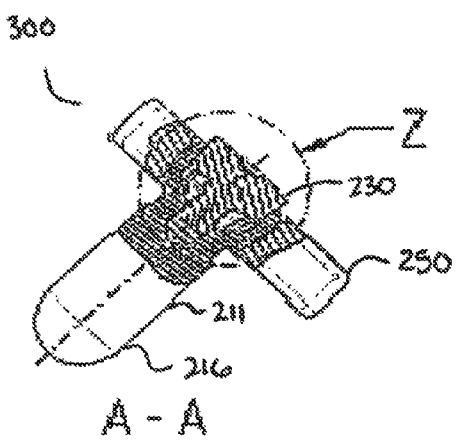
FIG. 9A  FIG. 9B

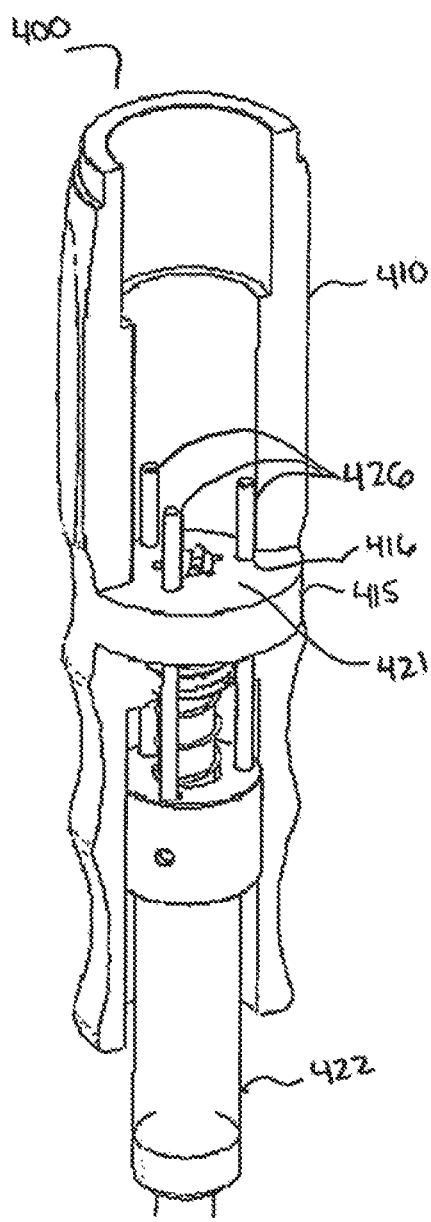
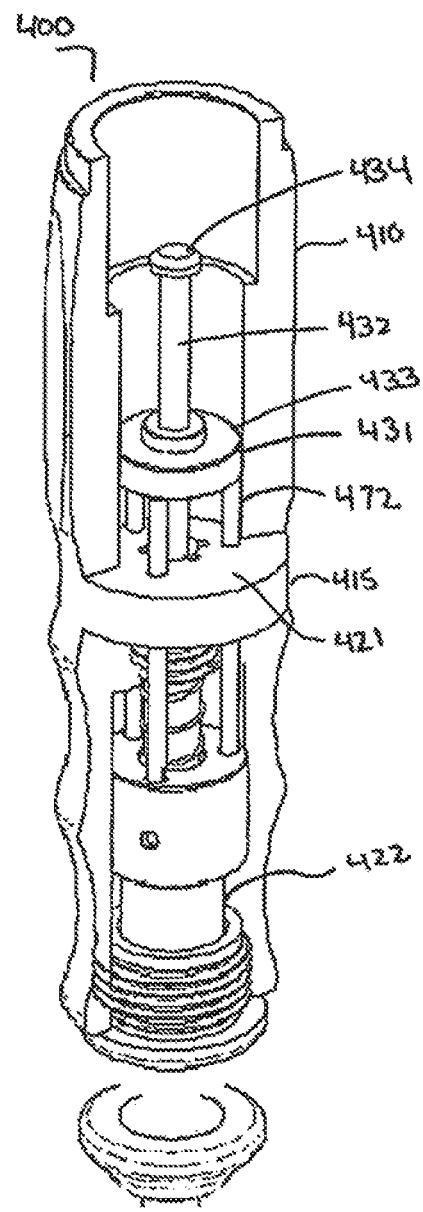
FIG. 10D
FIG. 10E

ORTHOPEDIC ANCHOR ASSEMBLY

REFERENCE TO RELATED APPLICATIONS

The present invention is a continuation application of U.S. Ser. No. 13/273,625, filed Oct. 14, 2011, which is herein incorporated by reference in its entirety.

FIELD OF THE INVENTION

The present invention is directed to a bone fixation assembly and, in particular, to an anchor assembly for securing an orthopedic device to bone tissue.

BACKGROUND OF THE INVENTION

In the field of orthopedic surgery, and more specifically spinal surgery, bone anchors may be used for fixation or for the fastening of orthopedic devices or instruments to bone tissue. An exemplary use of bone anchors may include using the bone anchors to fasten an orthopedic device, such as a bone plate, a spinal rod, or a spinal spacer, to a vertebral body for the treatment of a deformity or defect in a patient's spine. Focusing on the bone plate example, bone anchors can be secured to a number of vertebral bodies and a bone plate can then be connected to the vertebral bodies via the bone anchors to fuse a segment of the spine. In another example, bone anchors can be used to fix the location of a spinal spacer once the spacer is implanted between adjacent vertebral bodies. In yet another example, bone anchors can be fastened to a number of vertebral bodies to anchor a spinal rod in place along a spinal column to treat a spinal deformity.

In each of these exemplary uses, a plurality of bone anchors are needed to fasten the orthopedic device to the area of treatment. In addition, depending on the extent of the disease or size of the defect to be treated, it is possible that several orthopedic devices each requiring a plurality of bone anchors may be required. Accordingly, the fastening of the orthopedic implants to the area of treatment can become a time consuming and even difficult task.

As such, there exists a need for bone anchors that can quickly and securely fasten an orthopedic device to the area of treatment.

SUMMARY OF THE INVENTION

Various embodiments of orthopedic assemblies are provided. In some embodiments, an orthopedic assembly comprises a plate member having an aperture. An anchor is insertable through the aperture of the plate member. The anchor can include a plurality of arms separated by grooves. The assembly further comprises a locking mechanism insertable through the anchor. The locking mechanism can include a plurality of fingers corresponding to each of the arms. Downward insertion of the locking mechanism through the anchor causes the plurality of arms to splay outwardly to thereby secure the anchor to the plate member.

In some embodiments, an orthopedic assembly comprises a plate member having an aperture. An anchor is insertable through the aperture of the plate member. The anchor includes a plurality of arms, wherein each of the arms includes a slot formed in an inner wall. A locking mechanism is insertable through the anchor. The locking mechanism includes a plurality of fingers, wherein each finger is insertable into a slot of the anchor. Downward insertion of the locking mechanism through the anchor causes the plurality of arms to splay outwardly to thereby secure the anchor to the plate member.

In some embodiments, an orthopedic assembly comprises a plate member having an aperture. An anchor is insertable through the aperture of the plate member. A locking mechanism is insertable through the anchor. The locking mechanism is capable of expanding the anchor to secure the anchor to the plate member. An insertion instrument is further provided to deliver the locking mechanism to the anchor via an impaction process.

BRIEF DESCRIPTION OF THE DRAWINGS

The present invention will become more fully understood from the detailed description and the accompanying drawings, wherein:

FIG. 8A is a cross-sectional view of a first position of a locking mechanism in an anchor according to some embodiments.

FIG. 8B is a cross-sectional view of a second position of a locking mechanism in an anchor according to some embodiments.

FIG. 9A is a side view of an orthopedic device assembly according to some embodiments.

FIG. 9B is a cross-sectional view of the orthopedic device assembly in FIG. 9A.

FIGS. 10A-10I illustrate different views of a multi-functional insertion instrument according to some embodiments.

DETAILED DESCRIPTION OF THE ILLUSTRATED EMBODIMENTS

Figure 1:
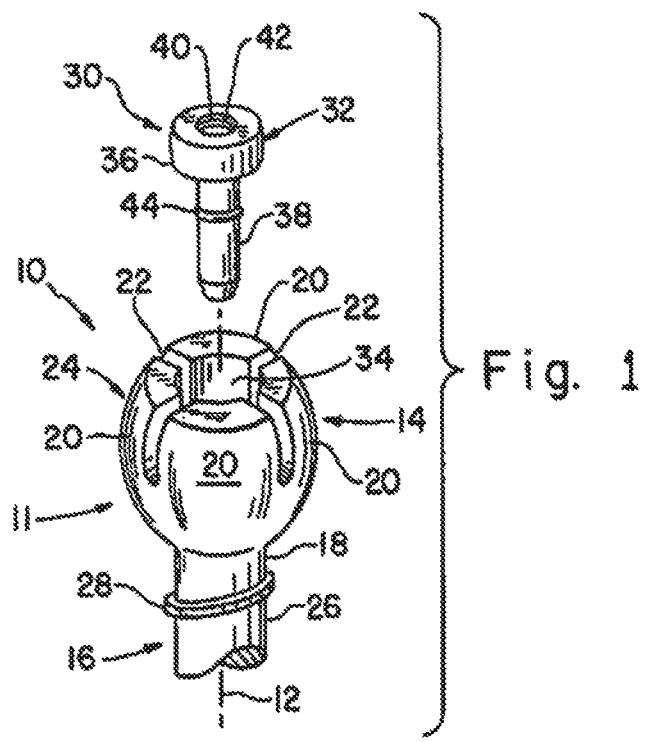
FIG. 1 is an exploded partial perspective view of one embodiment of an anchor assembly.

The following description of the preferred embodiments is merely exemplary in nature and is in no way intended to limit the invention, its application, or uses.

With reference to FIGS. 1-4, a preferred embodiment of an anchor assembly 10 is illustrated. The anchor assembly 10 preferably includes an anchor 11 and a locking mechanism 30. Although the anchor 11 will be discussed in the context of an orthopedic screw, it is contemplated that the anchor 11 can be any type of anchoring element including, but not limited to, a hook, a pin, or a nail. In a preferred embodiment, the anchor 11 includes, concentric to a longitudinal axis 12, a head portion 14, a neck portion 18 and a shank portion 16. The head portion 14 connects to the shank portion 16 through the neck portion 18. The anchor assembly 10 is preferably constructed from any biocompatible material including, but not limited to, stainless steel alloys, titanium, titanium based alloys, or polymeric materials.

In a preferred embodiment, the head portion 14 of the anchor 11 has a generally spherical shape and includes at least one resilient finger element 20. In another preferred embodiment, the head portion 14 includes four resilient finger elements 20. Preferably, located on either side of the resilient finger element 20 is an elongated groove 22. The grooves 22 may be configured and dimensioned to correspond with the end of a driving instrument (not shown) designed to engage the anchor 11, and consequently the anchor assembly 10.

Figure 4:
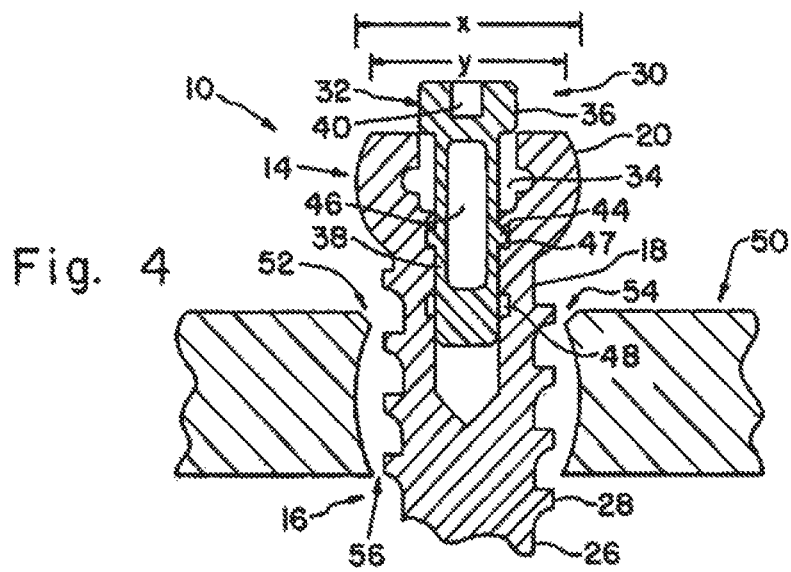
FIG. 4 is a partial cross-sectional view of the anchor assembly shown in FIG. 1.

As best shown in FIG. 4, the generally spherical shape of the head portion 14 is configured and dimensioned to be received within a correspondingly shaped cavity 52 in an orthopedic device 50 which may be part of a spinal fixation system. In an exemplary embodiment, the orthopedic device 50 is a bone plate, but the orthopedic device can be any device, such as a spinal rod "tulip" style holder or a spinal spacer. The shape of the head portion 14 and the correspondingly shaped cavity 52 allows the anchor assembly 10 to pivot, rotate and/or move with respect to the orthopedic device 50. In another embodiment, instead of allowing the anchor assembly 10 to pivot, rotate and/or move with respect to the orthopedic device 50, the head portion 14 and the correspondingly shaped cavity 52 may be configured and dimensioned to keep the anchor assembly 10 in a fixed position. In an exemplary use, the head portion 14 of the anchor 11 is received in the cavity 52 of the orthopedic device 50 and the anchor assembly 10 is pivoted, rotated or moved until the desired orientation with respect to the orthopedic device 50 is met. The anchor assembly 10 is then locked in place, which is discussed in detail below, in the cavity 52 of the orthopedic device 50. In a preferred embodiment, the head portion 14 also includes texturing 24 that extends along at least a portion of the head portion 14. The texturing 24 on the head portion 14 provides additional frictional surfaces which aid in locking the anchor assembly 10 in place with respect to the orthopedic device 50.

Turning back to FIGS. 1-3, in a preferred embodiment, the neck portion 18 of the anchor 11 integrally connects the head portion 14 with the shank portion 16. The diameter of the neck portion 18 is preferably dimensioned to match the minor diameter of the anchor 11. By having the diameter of the neck portion 18 dimensioned at least as large as the minor diameter of the anchor 11, the overall rigidity and strength of the anchor 11 is increased.

In a preferred embodiment, the shank portion 16 of the anchor 11 includes a shaft 26 surrounded at least in part by a thread portion 28. The diameter of the shaft 26 is the minor diameter of the anchor assembly 10. In a preferred embodiment, the diameter of the shaft 26 remains generally constant from a proximal end of the shaft 26 toward a distal end of the shaft 26. The constant diameter of a majority portion of the shaft 26 allows for optimal anchor positioning when the anchor assembly 10 is inserted into a predetermined area in the bone tissue. The constant diameter also allows for varying the depth positioning of the anchor assembly 10 in the bone. For example, if a surgeon places the anchor assembly 10 into bone tissue at a first depth and decides the placement is more optimal at a second, shallower depth, the anchor assembly 10 can be backed out to the second depth and still remain fixed in the bone. In another embodiment, the diameter of the shaft 26 may vary along its length, including increasing in diameter from the proximal end to the distal end or decreasing in diameter from the proximal end to the distal end.

Figure 2:
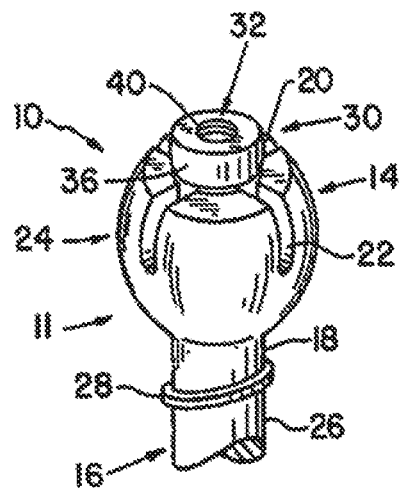
FIG. 2 is a partial perspective view of the anchor assembly shown in FIG. 1.
Figure 3:
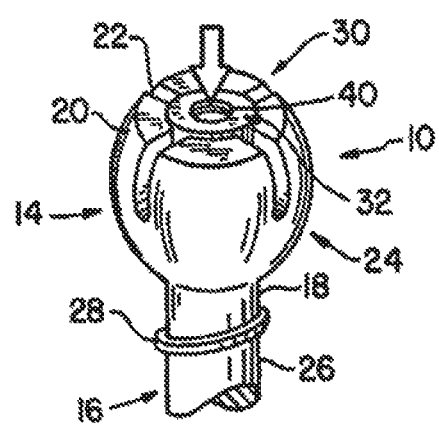
FIG. 3 is partial perspective view of the anchor assembly shown in FIG. 1.

With continued reference to FIGS. 1-3, the thread portion 28 surrounding the shaft 26 extends, in a preferred embodiment, from the distal end of the shaft 26 to the neck portion 18. In another preferred embodiment, the thread portion 28 may extend along only a portion of shaft 26. The thread portion 28 is preferably a Modified Buttress thread but the thread can be any other type of threading that is anatomically conforming, including, but not limited to Buttress, Acme, Unified, Whitworth and B&S Worm threads.

In a preferred embodiment, the diameter of the thread portion 28 decreases towards the distal end of the anchor 11. By having a decreased diameter thread portion 28 near the distal end of the anchor 11, the anchor 11 can be self-starting. In another preferred embodiment, anchor 11 may also include at least one flute to clear any chips, dust, or debris generated when the anchor assembly 10 is implanted into bone tissue.

Looking again at FIGS. 1-4, the anchor assembly 10 preferably includes the locking mechanism 30. In a preferred embodiment, the locking mechanism 30 will lock the anchor assembly 10 with respect to the orthopedic device 50 thereby preventing the anchor assembly 10 from disengaging from the orthopedic device 50. The locking mechanism 30 preferably includes a locking member 32 which is configured and dimensioned to be received in an opening 34 in the anchor 11.

In a preferred embodiment, the locking member 32 has a head member 36 and a shaft member 38. The head member 36 preferably includes an opening 40 for receiving a driving instrument (not shown). The opening 40 may also include threading 42 that is capable of threadingly engaging a driving instrument for reasons explained below. In a preferred embodiment, the shaft member 38 includes at least one protrusion 44 extending along at least a portion of the circumference of the shaft member 38. Focusing on FIG. 4, at least a portion of the shaft member 38, in a preferred embodiment, also includes a hollow portion 46 which allows at least a portion of the shaft member 38 surrounding the hollow portion 46 to flex inwardly.

Turning back to FIGS. 1 and 4, the opening 34, preferably, is generally annular and extends coaxially with the longitudinal axis 12 from the head portion 14 through the neck portion 18 into the shank portion 16. The opening 34 preferably also includes at least two recesses 47, 48, each recess 47, 48 extending along at least a portion of the circumference of the opening 34. Each recess 47, 48 is configured and dimensioned to accommodate the protrusion 44.

In an exemplary use of the anchor assembly 10 with the orthopedic device 50, the orthopedic device 50 is first oriented and placed in the area of treatment. The orthopedic device 50 is then fastened to the bone tissue via at least one anchor assembly 10 which is received in at least one cavity 52 of the orthopedic device 50. Looking at FIG. 4, in a preferred embodiment, the cavity 52 has a generally spherical shape with a first diameter y at an upper portion 54. When viewed from the upper portion 54 to a lower portion 56, the diameter of the cavity 52 generally increases until approximately the middle portion of the cavity 52. The diameter of the approximately middle portion of the cavity 52 is a second diameter x. The diameter of the cavity 52 then decreases from the approximately middle portion of the cavity 52 to the lower portion 56, where the diameter of the cavity near the lower portion 56 is the same as or smaller than the first diameter y.

In a preferred embodiment, the anchor assembly 10 passes through the cavity 52 until the head portion 14 of the anchor 11 abuts the top portion 54 of the cavity 52. As can be seen in FIG. 4, in a preferred embodiment, the diameter of the head portion 14 of the anchor 11 is generally the same width as diameter x. Since the top portion 54 of the cavity 52 has a diameter y, which is smaller than the diameter x, as the head portion 14 is brought into the cavity 52, the finger elements 20 of the head portion 14 resiliently bias inwardly reducing the diameter of the head portion 14 until the head portion 14 fits through top portion 54 of the cavity 52. Once the head portion 14 passes through the top portion 54, the resilient finger elements 20 return back to their original position as the head portion 14 is seated in the cavity 52.

As best seen in FIGS. 3 and 4, in a preferred embodiment, once the anchor assembly 10 is seated in the cavity 52, the anchor assembly 10 can be locked in the cavity 52 by actuating the locking mechanism 30. In a preferred embodiment, a user actuates locking mechanism 30 by pushing on the head member 36 of the locking member 32. The downward force moves the locking member 32 further into the opening 34. As the locking member 32 moves into the opening 34, the protrusion 44 will disengage from the recess 47. Since, in a preferred embodiment, the diameter of the shaft member 38 of the locking member 32 is generally equivalent to the diameter of the opening 34 near the neck portion 18 and the shaft portion 16, the shaft member 38 will flex inwardly, aided by the hollow portion 46, to accommodate the protrusion 44 once it disengages from the recess 47. The locking member 32 will continue to move further into opening 34 until the protrusion 44 engages the recess 48 at which point the head member 36 will be seated between the resilient finger elements 20 of the head portion 14. The anchor assembly 10 is now locked in the cavity 52 since the head member 36, once seated between the resilient finger elements 20, prevents the resilient finger elements 20 from flexing inwardly. It is important to note that the disengagement of protrusion 44 from recess 47 and the engagement of the protrusion 44 with the recess 48 (and vice versa) provides the user with audible and/or tactile feedback allowing the user to quickly and easily confirm the locked or unlocked status of the anchor assembly 10.

As mentioned earlier, the head portion 36 includes the opening 40 which may include threading 42. The threading 42 in opening 40 engages a driving instrument (not shown) allowing a user to pull on the locking mechanism 30 thereby unlocking the anchor assembly 10 in the event a user wants to disengage the anchor assembly 10 from the orthopedic device 50.

In another exemplary use of the anchor assembly 10 with the orthopedic device 50, the orthopedic device 50 is first oriented and placed in the area of treatment. The orthopedic device 50 is then fastened to the bone tissue via at least one anchor assembly 10 which is received in at least one cavity 52 of the orthopedic device 50. In this exemplary use, after the anchor assembly 10 is seated in the cavity 52, but before the anchor assembly 10 is locked in the cavity 52, the anchor assembly 10 is pivoted, rotated or otherwise moved until the desired orientation with respect to the orthopedic device 50 is met. The anchor assembly 10 is then locked in place at that desired orientation by actuating the locking mechanism 30 as discussed above.

In this exemplary use, to lock the anchor assembly 10 at the desired orientation another preferred embodiment of the anchor assembly 10, and more specifically, another preferred embodiment of the locking mechanism 30 is necessary. In this preferred embodiment, the locking mechanism 30 is configured and dimensioned to resiliently bias the resilient finger elements 20 of head portion 14 outwardly when the locking mechanism 30 is pushed from the first, unlocked position, to the second, locked position. By resiliently biasing the finger elements 20 outwardly, the finger elements 20 will push against the walls of the cavity 52 thereby locking the anchor assembly 10 in place in the desired orientation. To resiliently bias the finger elements 20 outwardly, the head member 36 of the locking mechanism 30, preferably, is configured and dimensioned to include tapering surfaces and a diameter larger than the diameter of the opening 34 near the head portion 14.

Figure 5:
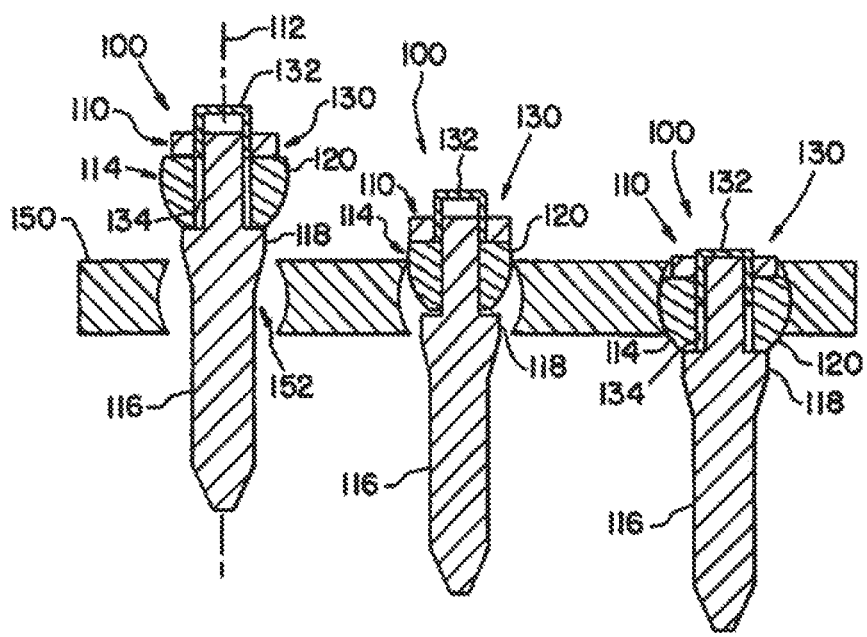
FIG. 5 is a schematic view of another embodiment of an anchor assembly being seated and locked in an orthopedic device.

Turning to FIG. 5, a preferred embodiment of the anchor assembly 100 is shown. The anchor assembly 100 is similar to anchor assembly 10, as such, only the differences between the two embodiments are addressed herein. The anchor assembly 100 preferably includes an anchor 110 and a locking mechanism 130. In a preferred embodiment, the anchor 110 includes, concentric to a longitudinal axis 112, a head portion 114, a neck portion 118 and a shank portion 116. The head portion 114 connects to the shank portion 116 through the neck portion 118. In a preferred embodiment, the head portion 114 of the anchor 110 has a generally spherical shape and includes a resilient ring element 120 captured between an upper and lower end of the head portion 114.

With continued reference to FIG. 5, in a preferred embodiment, the locking mechanism 130 will lock the anchor assembly 100 with respect to the orthopedic device 150 thereby preventing the anchor assembly 100 from disengaging from the orthopedic device 150. The locking mechanism 130 preferably includes a locking member 132 which is configured and dimensioned to be received in an opening 134 in the anchor 110.

In an exemplary use of the anchor assembly 100 with the orthopedic device 150, the orthopedic device 150 is first oriented and placed in the area of treatment. The orthopedic device 150 is then fastened to the bone tissue via at least one anchor assembly 100 which is received in at least one cavity 152 of the orthopedic device 150. In a preferred embodiment, the anchor assembly 100 passes through the cavity 152 until the head portion 114 of the anchor 110 abuts a top portion of the cavity 152. Since the top portion of the cavity 152 has a diameter that is smaller than the diameter of the head portion 114, to fit the head portion 114 into the cavity 152, the resilient ring 120 is resiliently bias inwardly, reducing the diameter of the head portion 114, until the head portion 14 fits through top portion of the cavity 152. Once the head portion 114 passes through the top portion of the cavity 152, the ring 120 returns back to its original position as the head portion 114 is seated in the cavity 152.

With continued reference to FIG. 5, in a preferred embodiment, once the anchor assembly 100 is seated in the cavity 152, the anchor assembly 100 can be locked in the cavity 152 by actuating the locking mechanism 130. In a preferred embodiment, a user actuates locking mechanism 130 by pushing on the locking member 132. The downward force moves at least a portion of the locking member 132 into opening 134. The anchor assembly 100 is now locked in the cavity 152 since the locking member 132, once seated in the opening 134, prevents the ring 120 from flexing inwardly.

Additional Embodiments of Locking Bone Screw Assemblies

Additional embodiments of an alternative locking bone screw assembly including an anchor and locking mechanism are described. The assembly allows the anchor to be secured to an orthopedic device, such as a bone plate. The alternative locking bone screw assembly comprises an anchor with splaying arms and an insertable locking mechanism that forces the arms to splay, thereby expanding the arms of the anchor. When the arms of the anchor are expanded, the arms press against the surface of the orthopedic device, thereby causing fixation between the anchor the orthopedic device. For example, the anchor can be positioned in an aperture of an orthopedic plate member. Before expansion of the anchor, the anchor is free to move about in multiple orientations and directions relative to the orthopedic plate. Following expansion, the walls of the anchor are pressed firmly against the walls of the orthopedic plate member, thereby helping to retain the anchor within the plate member and form an assembly. In other words, in some embodiments, there is no locking interference between the anchor and the orthopedic plate member prior to expansion and splaying of the anchor. After the walls of the anchor have been splayed into a different locking diameter, the anchor is securely fixed to the plate member. The advantage of this assembly is that it includes a locking mechanism that does not require an axial force to overcome a locking element or a certain amount of thread purchase to operate the locking feature. In addition, the position of the locking mechanism provides a clear visual indication of whether the anchor is locked or unlocked. Moreover, the anchor can be easily removed from the orthopedic device without ruining the orthopedic device using the locking mechanism described herein.

Figure 6A:
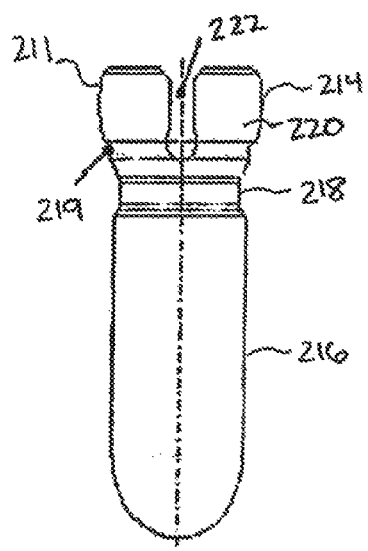
FIG. 6A is a side view of an alternative anchor according to some embodiments.

FIG. 6A is a side view of an alternative anchor according to some embodiments. The anchor 211 includes a head portion 214, a neck portion 218 and a shank portion 216. The anchor 211 is designed to fit through an aperture of an orthopedic device (e.g., a plate member) to secure the device to a treatment site.

Figure 6B:
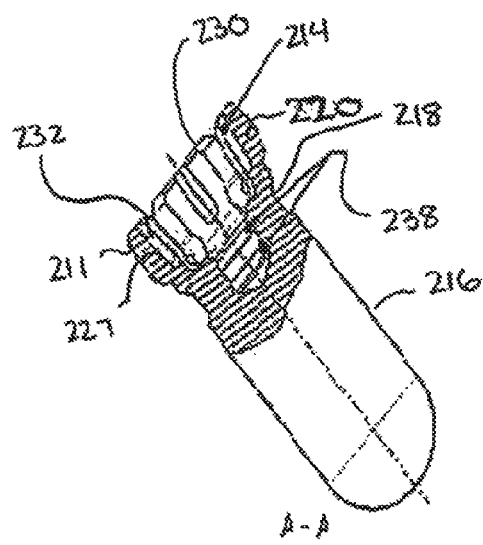
FIG. 6B s a cross-sectional view of the anchor in FIG. 6A with an alternative locking mechanism according to some embodiments.
Figure 6C:
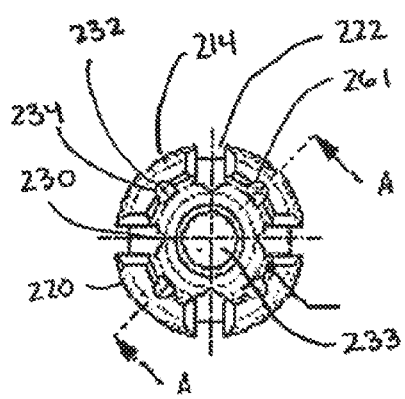
FIG. 6C is a top view of the anchor and locking mechanism in FIG. 6B.

The anchor head portion 214 comprises an upper opening for receiving a locking mechanism 230, as shown in FIG. 6C. The head portion 214 comprises two or more resilient members in the form of fingers or arms 220 that are separated by grooves 222. In the illustrated embodiment, the head portion 214 comprises four arms 220, each of which is separated by a single groove. The arms 220 are advantageously capable of splaying outwardly from a central axis of the anchor 211 when a force is applied. In some embodiments, the splaying force can be applied by inserting a locking mechanism 230 having splay fingers 232 (shown in FIGS. 7A-7C) into the head portion 214. The locking mechanism 230 forces the outward expansion of the arms 220 of the head portion 214.

While in the illustrated embodiment, the head portion 214 comprises four arms 220 separated each by a groove 222, such that each adjacent groove 222 is at approximately a 90 degree angle from one another, the head portion 214 can also include other configurations. For example, the head portion 214 can include three arms, each of which is separated by grooves. In this situation, adjacent grooves can be approximately 120 degrees away from another. In some embodiments, more than four arms 220 are formed in the head portion, such as five, six, seven, eight or more. In addition, the adjacent grooves 222 can also be separated by greater than or less than 90 degree angles. Moreover, while the grooves 222 are illustrated as symmetrical, in other embodiments, the grooves 222 are asymmetrical.

The anchor head portion 214 transitions into the shank portion 216 via the neck portion 218. In some embodiments, the neck portion 218 includes one or more relief cuts 219 that are machined along at least a portion of the neck. The relief cuts 219 advantageously accommodate and facilitate the splaying of the arms 220 of the head portion. The orientation of the relief cuts 219 allows the arms to splay easier in their outward directions. In some embodiments, the relief cuts 219 are positioned at a bottom end of a pocket of the anchor head to enhance the ability of arms to flex outwardly away from the central axis of the anchor.

The shank portion 216 comprises an extended shaft that can be inserted into a bone member. While the shank portion 216 is illustrated as having no threads, in other embodiments, the shank portion 216 comprises a plurality of threads that extend along at least a portion of its length. The threads can be single diameter threads or dual diameter threads.

FIG. 6B s a cross-sectional view of the anchor 211 in FIG. 6A with a locking mechanism 230 inserted therein according to some embodiments. The locking mechanism 230 includes a plurality of splay fingers 232, each of which engages an inner wall 227 of at least one arm 220 of the head portion 214. In some embodiments, one or more of the inner walls 227 of the head portion arms 220 include a groove or slot 234 for receiving a splay finger of the locking mechanism 230, as shown in FIG. 6C. As the locking mechanism 230 is inserted downwardly into the head portion 214, the splay fingers 232 of the locking mechanism slide down the slots 234 in the head portion and force the head portion to splay and expand outwardly. In some embodiments, the splay fingers 232 of the locking mechanism are tapered. The slots 234 for receiving the splay fingers 232 in the anchor can also be tapered. Advantageously, in addition to facilitating the splaying of the anchor arms, the slots 234 in the anchor 211 also assist in guiding the locking mechanism 230 into the proper orientation within the anchor 211.

FIG. 6C is a top view of the anchor and locking mechanism in FIG. 6B. As shown from this viewpoint, the splay fingers 232 of the locking mechanism 230 are slidably inserted into the slots 234 along the inner wall of the anchor arms 220, thereby forcing outward expansion of the head of the anchor.

The top of the locking mechanism 230 is visible in FIG. 6C. As shown in the figure, the top of the locking mechanism 230 can include a central circular portion 233 that is suitable for instrument engagement. In addition, the central circular portion 233 of the locking mechanism 230 advantageously maintains a centralized locking force between the locking mechanism 230 and the anchor 211, thereby allowing for an equal force distribution amongst the splay fingers 232.

Figure 7A:
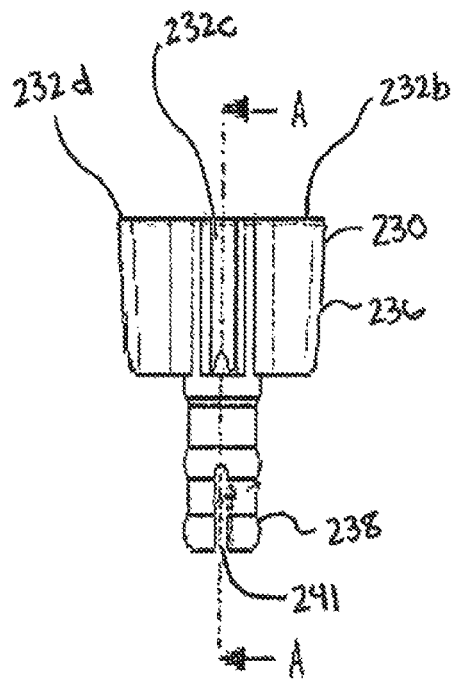
FIG. 7A is a side view of an alternative locking mechanism according to some embodiments.
Figure 7B:
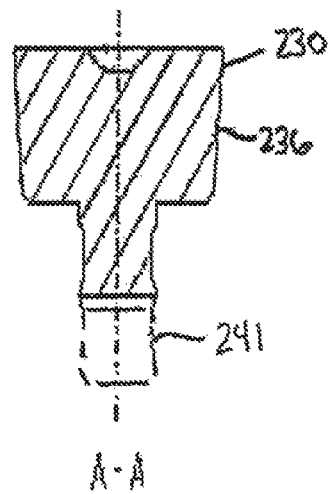
FIG. 7B is cross-sectional view of the locking mechanism in FIG. 7A.

FIG. 7A is a side view of an alternative locking mechanism according to some embodiments. The locking mechanism 230 includes an upper head portion 236 comprising one or more splay fingers 232 and a lower shaft portion 238. In the illustrated embodiment, the locking mechanism 230 includes four splay fingers 232a, 232b, 232c and 232d. The splay fingers 232 engage the inner walls of the arms of the anchor head, thereby promoting splaying of the anchor head.

As shown in FIG. 7A, the lower shaft portion 238 of the locking mechanism can include one or more compression slots 241. In the illustrated embodiment, the compression slot 241 extends from a point within the shaft portion 238 to a distal end of the shaft portion 238. When the locking mechanism 230 is inserted into the anchor 211, the lower shaft portion 238 can compress against inner walls of the anchor (as shown in FIG. 6B), thereby advantageously facilitating insertion of the locking mechanism 230 within the anchor 211.

Figure 7C:
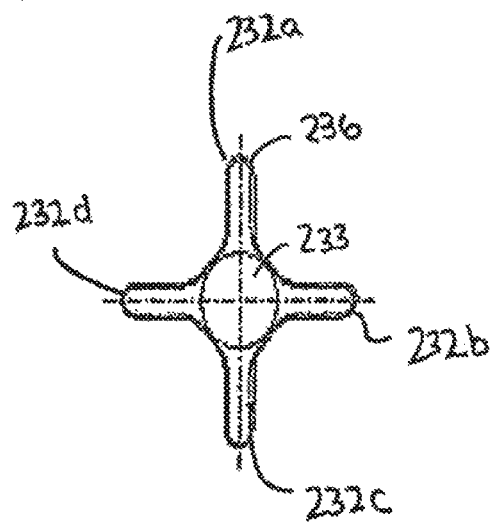
FIG. 7C is a top view of the locking mechanism in FIG. 7A.

FIG. 7C is a top view of the locking mechanism in FIG. 7A. The splay fingers 232a, 232b, 232c and 232d are illustrated as symmetrical about the central circular portion 233. This symmetry advantageously allows forces to be evenly distributed around the locking mechanism. In other embodiments, the splay fingers 232 need not be symmetrical about the central circular portion.

FIG. 8A is a cross-sectional view of a first position of a locking mechanism 230 in an anchor 211 according to some embodiments. As shown in the figure, portions of the outer arms 220 of the anchor 211 contact the inner walls of an orthopedic device in the form of a plate 250; however, as the locking mechanism 230 is not fully inserted down through the anchor 211, the arms 220 of the anchor are not splayed outwardly and thus, the anchor 211 is free to move about relative to the plate 250. In this first position, the locking mechanism 230 is in the process of being inserted into the head portion of the anchor 211. As shown in the figure, the top of the locking mechanism 230 is proud above a top surface of the anchor 211. In this first position, the arms 220 of the anchor 211 are not yet fully splayed and pressed firmly against the inner wall, such that the orientation and position of the anchor 211 can still be adjusted relative to the plate 250.

FIG. 8B is a cross-sectional view of a second position of a locking mechanism 230 in an anchor 211 according to some embodiments. In this figure, the locking mechanism 230 has been inserted further down the anchor 211, thereby forcing the arms 220 of the anchor to splay outwardly. When the anchor arms 220 are splayed outwardly, they press against the inner walls of the plate 250, thereby forming a secure fit. The position and angle of the anchor 211 is thus fixed relative to the plate 250, thereby forming a secure assembly.

FIG. 9A is a side view of an orthopedic device assembly 300 according to some embodiments. The assembly 300 comprises a plate member 250 secured to an anchor 211. By inserting a locking mechanism 230 into an upper opening of the anchor 211, arms of the anchor can splay outwardly, thereby securing the anchor 211 to the plate member 250.

FIG. 9B is a cross-sectional view of the orthopedic device assembly in FIG. 9A. From this viewpoint, one skilled in the art can appreciate that the locking mechanism 230 is in the process of being fully inserted into anchor 220 to thereby secure the anchor 220 to the plate member 250.

Methods of using the locking assembly are now provided. In some embodiments, an orthopedic device, such as a plate member, can be oriented and placed in an area of treatment. The orthopedic device includes one or more apertures for receiving anchor members to secure the orthopedic device to the treatment area. An anchor member can be inserted through an aperture of the orthopedic device. The anchor member is free to move in different positions and/or orientations relative to the orthopedic device until a locking mechanism is inserted therein. The locking mechanism can comprise one or more splaying arms that engage the inner walls of the anchor member, thereby causing expansion of the anchor member within the orthopedic device. Once the anchor member is expanded, the anchor member is secured to the orthopedic device, thereby forming a secure assembly.

Multi-Functional Instruments

Novel instruments are now described that cooperate with the locking bone screw assemblies described above, and in particular, those in FIGS. 6A-9B. The instruments are advantageously multi-functional and can help to both drive an anchor into a bone member and provide the locking mechanism to secure the anchor to an orthopedic device such as a plate member. The multi-functional instruments can advantageously provide a novel "impact to lock" feature that secures the anchor to orthopedic device.

FIGS. 10A-10I illustrate different views of a multi-functional insertion instrument according to some embodiments. The insertion instrument 400 comprises a proximal portion 402 comprising a handle 410 and a distal portion 405. The distal portion 405 can hold a locking mechanism, such as those shown in FIGS. 7A-7C.

The multi-functional insertion instrument 400 is configured to advantageously accommodate three different features: a drive feature, a cocking/setting feature and a catch and release feature. The drive feature allows an anchor, such as that shown in FIGS. 6A-6C, to be driven into a bone member. The cocking feature prepares a locking mechanism, such as that shown in FIGS. 7A-7C, for impaction into the anchor so as to secure the anchor to an orthopedic device. The catch and release feature operates with the cocking feature, and serves to forcefully release the locking mechanism into the anchor. The catch and release feature uses an impaction force to drive the locking mechanism into the anchor, thereby causing expansion of the anchor to secure the anchor to an orthopedic device. The instrument thus relies on a novel "impact to lock" concept that is not found in other instruments. The features of the instrument 400 that support these multiple features are now discussed in detail.

Figure 10A:
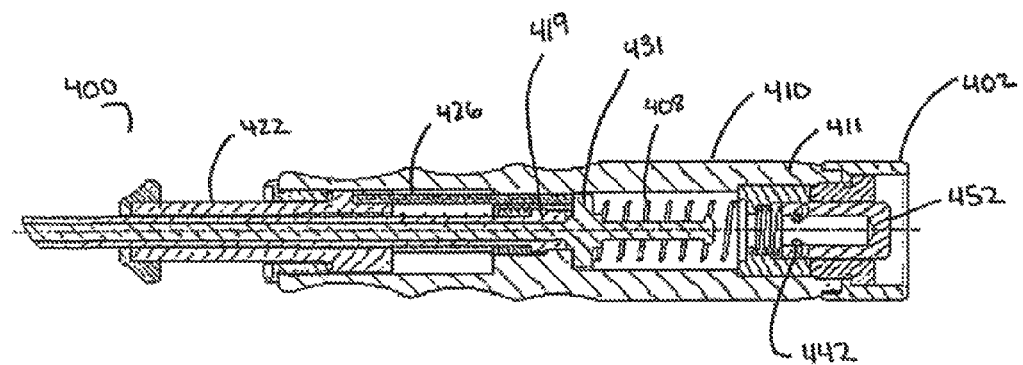
Figure 10B:
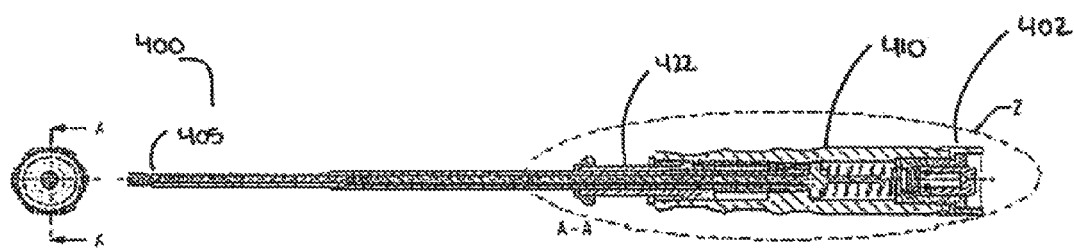

FIG. 10A illustrates a side cross-sectional view of the multi-functional insertion instrument 400. As shown in the figure, a number of features are enclosed within a housing 411 of the handle 410 in a proximal portion 402 of the instrument. A drive shaft 419, which relates to the drive feature, extends from within the handle 410 to a distal portion 405 (shown in FIG. 10B) of the instrument. A cocking sleeve 422 also extends from within the handle 410 to a more distal portion outside of the handle of the instrument. The cocking sleeve 422 moves in contact with one or more cocking pins 426 to move a hammer shaft 431 axially along the instrument. The cocking pins 426 and hammer shaft 431 are fully contained within the handle 410. The cocking sleeve 422, cocking pins 426, and hammer shaft 431 relate to the cocking feature that prepares a locking mechanism for impact to lock. The hammer shaft 431 interacts with catch pins 442 which capture the hammer shaft prior to impact to lock. A button 452 is provided to release the hammer shaft 431 from the catch pins 442, thereby forcing a locking mechanism on a distal end of the instrument 400 into an anchor. The catch pins 442 and button 452 thus relate to the release feature of the instrument.

Figure 10C:
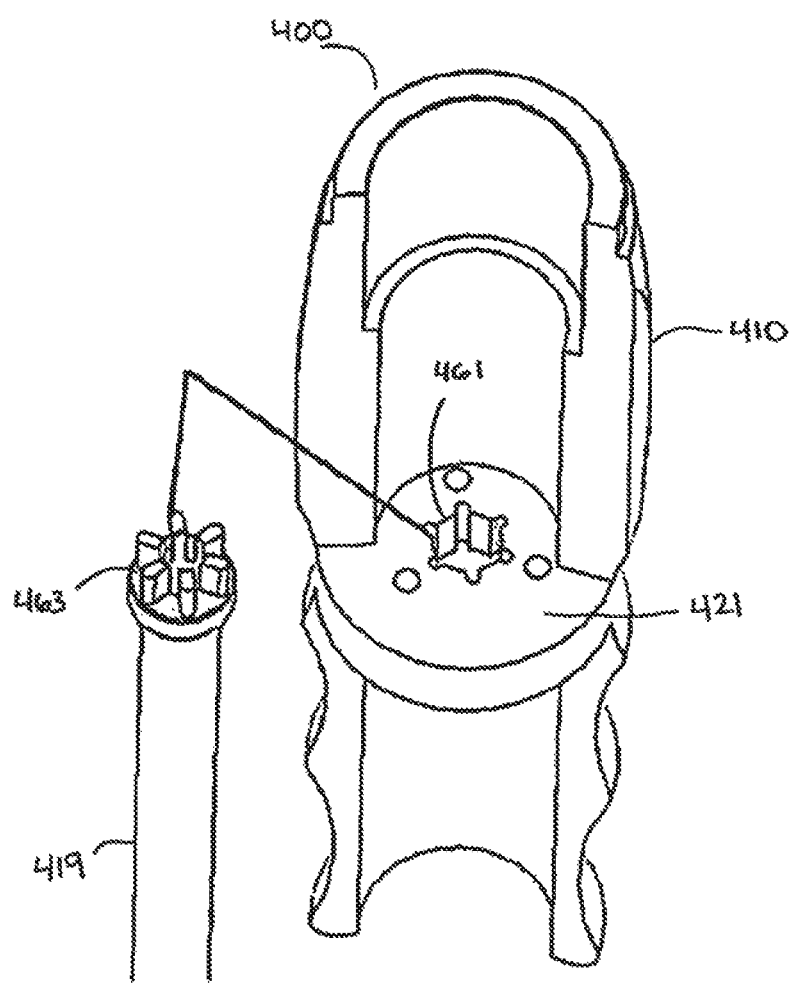

Instrument components related to the drive feature are shown in FIG. 10C. FIG. 10C illustrates a perspective view of an interior section of the handle 410, as well as a drive shaft 419 that extends through the interior section. The drive shaft 419, which can be used to drive an anchor into bone, includes a keyed pattern portion 463 that mates with a complementary keyed pocket 461 formed on a flat surface 421 within the handle 410. While in the illustrated embodiment, the keyed pattern portion 463 of the drive comprises a plurality of extending protrusions, other designs are also possible so long as it mates and aligns with the keyed pocket 461. For example, in some embodiments, the pattern portion can comprise a parallelogram with a plurality of edges that rests in a complementary pocket within the handle. The alignment between the keyed pattern portion 463 of the drive and the keyed pocket 461 within the handle advantageously provides an anti-torsion feature that allows the handle 410 to rotate and drive an anchor into bone, while still maintaining the ability to perform the cocking feature and catch and release feature discussed above.

Instrument components related to the cocking feature are shown in FIGS. 10D and 10E. FIG. 10D illustrates a perspective cross-sectional view of an interior section of the handle 410, including a cocking sleeve 422 and cocking pins 426. FIG. 10E also illustrates a perspective cross-sectional view of an interior section of the handle 410 and further includes the shaft hammer 431.

As shown in FIG. 10D, the instrument 400 includes a cocking shaft 422 that extends beyond a distal portion of the handle. The cocking shaft 422 is configured to move up and down axially along a length of the handle. In some embodiments, the cocking shaft 422 is operated manually, such as by fingers of a user.

The cocking shaft 422 is operably connected to a plurality of cocking pins 426. The cocking pins 426 extend through machined holes 416 formed in the flat surface 421 within the handle. Axial movement of the cocking shaft 422 simultaneously moves the cocking pins 426 along a length of the handle. While the illustrated embodiments illustrates three cocking pins 426, more or less than three pins can be provided to assist in setting the instrument.

Figures 10F, 10G:
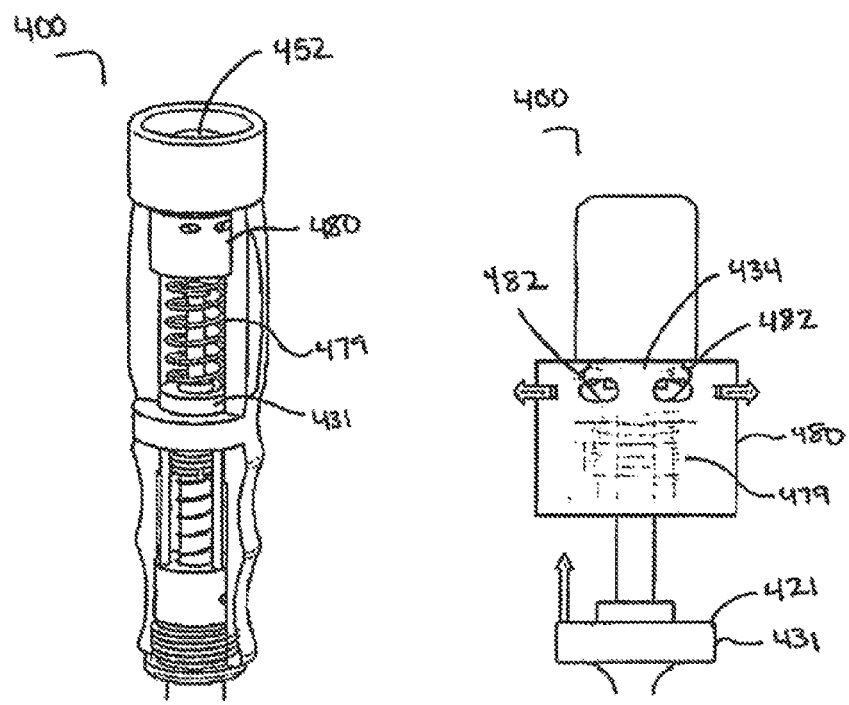

As shown in FIG. 10E, the top portion of the cocking pins 426 can contact the hammer shaft 431. The hammer shaft 431 comprises a disc portion 433 with an extended shaft 432 therein. The upper portion 434 of the hammer shaft 431 is chamfered to aid in the splaying of the catch pins, as shown in FIG. 10G. The distal portion of the hammer shaft 431 (not shown) is attached to a locking mechanism, such as that shown in FIG. 7A. When the cocking pins 426 move axially upward along the handle, the cocking pins 426 can push up against the bottom of the disc portion 433 of the hammer shaft 431, thereby causing the hammer shaft 431 to move upwards. As the hammer shaft 431 moves upwards, it is placed into a "firing position," whereby it is captured and then released to perform an impact to lock feature, as discussed below.

Figures 10H, 10I:
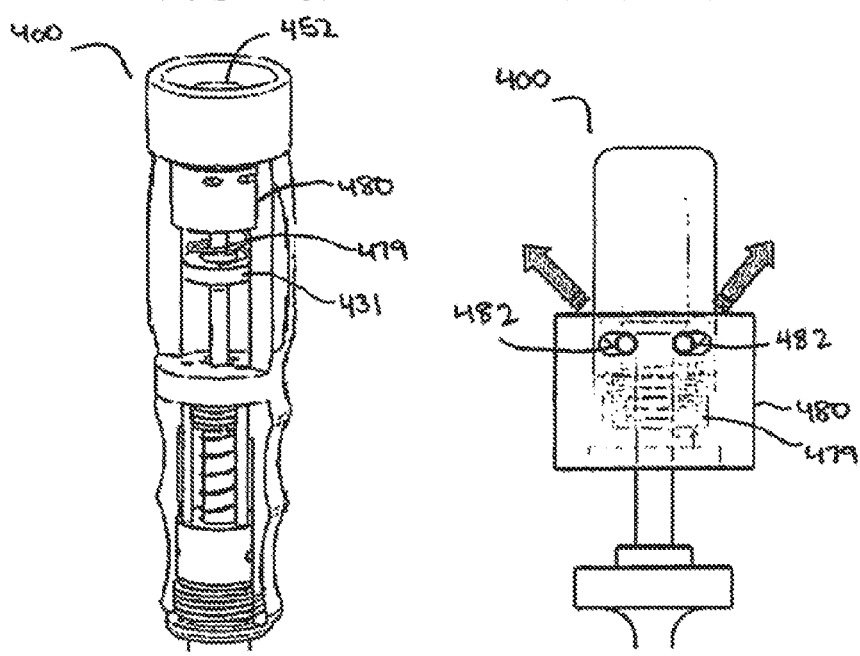

Instrument components related to the catch and release feature are shown in FIGS. 10E-10I. FIG. 10F illustrates a perspective cross-sectional view of the hammer shaft 431 prior to setting the hammer shaft into a firing position. FIG. 10G illustrates a front schematic view of the hammer shaft 431 in the process of being loaded into a firing position with the assistance of catch pins 482. FIG. 10H illustrates a perspective cross-sectional view of the hammer shaft 431 in the process of being loaded into a firing position. FIG. 10I illustrates a front schematic view of the hammer shaft 431 in the process of being released or fired.

The catch and release feature of the instrument 400 relies on one or more catch pins 482 which travel in a set of grooves, one of which is positioned in the housing perpendicular to a central longitudinal axis and another which is positioned proximate a release button. The catch pins 482 are designed to capture the upper portion 434 of the hammer shaft 431 to retain the hammer shaft 431 prior to release and impaction. As shown in FIG. 10G, as the hammer shaft 431 moves upwardly, the upper portion 434 of the hammer shaft 431 pushes and contacts the catch pins 482. The chamfered surfaces of the upper portion 434 advantageously aid in the perpendicular splaying of the catch pins 482, as shown in FIG. 10G. After splaying outwardly, the catch pins 482 return to capture a bottom section of the upper portion 434 of the hammer shaft 434, thereby capturing and retaining the hammer shaft 431 in a position prior to firing and release. When the hammer shaft 431 is ready for release, the release button 452 can be pushed. Pushing the release button 452 causes the pins to 482 to splay outwardly at an angle away from a central longitudinal axis of the instrument 400, as shown in FIG. 10, thereby causing the hammer shaft 431 to be released from capture. The released hammer shaft 431 drops downwardly to impact and lock the locking mechanism into the anchor, thereby securing the anchor to the orthopedic device.

As shown in FIGS. 10E-10I, the hammer shaft 431 can comprise a spring member 479 positioned between the lower flat surface 421 and the upper chamfered portion 434 of the hammer shaft 431. Accordingly, the hammer shaft 431 can comprise a spring-loaded device that is capable of capture and release to force impact of the locking mechanism into the anchor.

Advantageously, the instrument 400 can thus serve to both insert an anchor into a bone member and to secure the anchor to an orthopedic device. Both of these functions can be performed simultaneously or alternatingly.

Figure 11A:
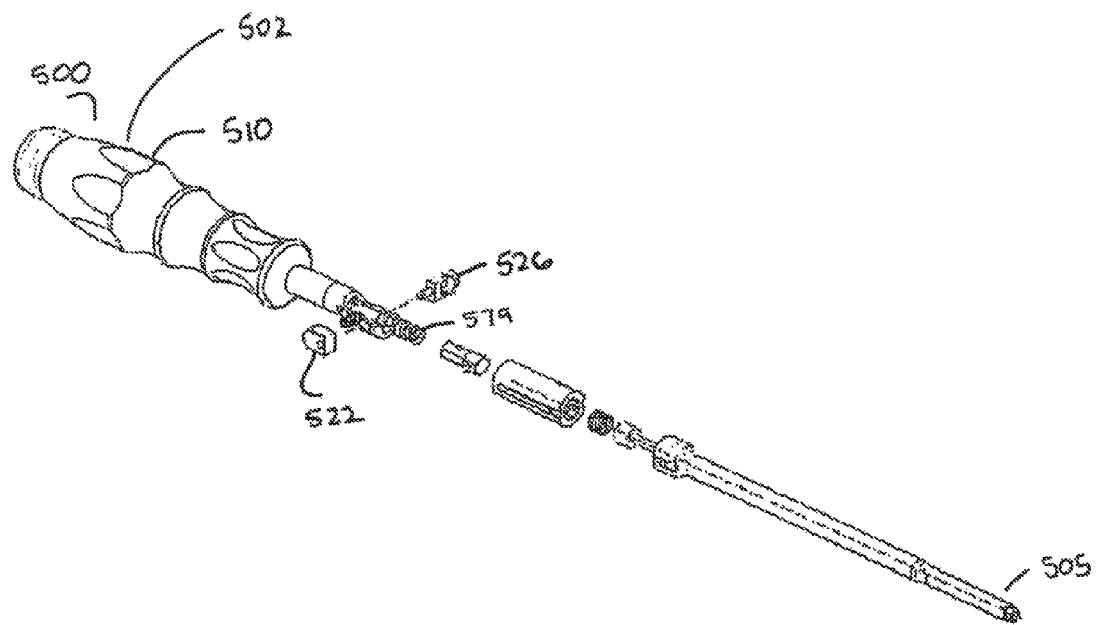
FIGS. 11A and 11B illustrate different views of an alternative multi-functional insertion instrument according to some embodiments.
Figure 11B:
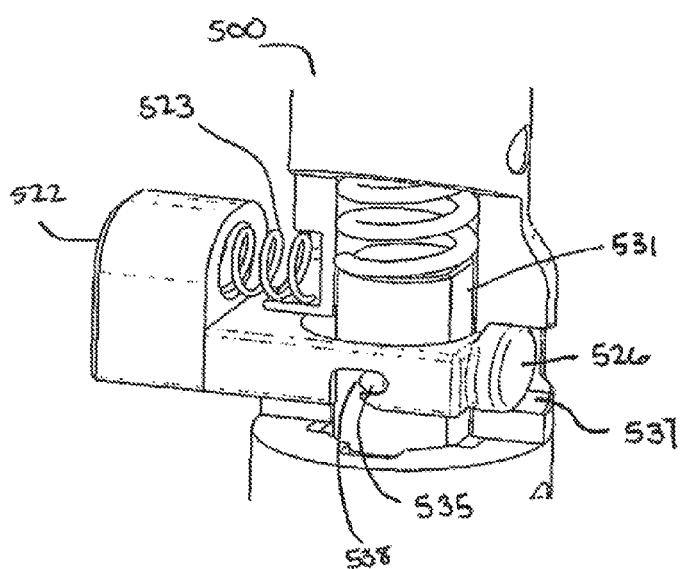

FIGS. 11A and 11B illustrate different views of an alternative multi-functional insertion instrument according to some embodiments. Like the previously described insertion instrument, the insertion instrument 500 is configured to both drive an anchor into a bone member and to impact a locking mechanism into the anchor to secure the anchor to an orthopedic device. However, unlike the previously described insertion instrument, instrument 500 includes a catch and release feature that is positioned outside of the handle body. FIG. 11A illustrates a perspective view of the insertion instrument 500, while FIG. 11B illustrates a close-up of the external catch and release feature of the instrument 500.

As shown in FIG. 11A, the insertion instrument 500 includes a proximal portion 502 comprising a handle and a distal portion 505. The distal portion 505 can grasp a locking mechanism to impact into an anchor (not shown). Within the proximal portion, a hammer shaft 531 can move upwardly. The hammer shaft 531 can operate with a spring or coil member 579 to generate spring-loaded forces to impact a locking mechanism into an anchor.

The catch and release feature of the insertion instrument is shown up close in FIG. 11B. The catch and release feature comprises a catch member 526 and a release member 522 that are operably connected and move together as a unit. The catch member 526 includes a catching location 538 for catching a pin member 535 on the hammer shaft 531. The release member 526 includes a release spring 523 that cooperates with the catch member 526. As the hammer shaft 531 is moved upwardly, the pin member 535 can be received in the catching location 538 of the catch member 526 in preparation for release and impaction.

As shown in FIG. 11B, the catch member 526 includes a flange that acts as a stop for release member 522. The assembly includes a counterbore 537 in the handle 510 that accepts the flange and acts as a stop with the flange. To cock and set the instrument, the hammer shaft 531 is pushed axially upwards towards the handle 510. During this movement, the release spring 523 is compressed, thereby moving the catch member 526 off the main axis. This movement allows the pin member 535 of the catch member to gain access to the groove formed in the catching location 538. At this point, the hammer shaft 531 is prepared for release and impaction. To release the hammer shaft 531, the release member 526 can be pushed, thereby moving the catch member until the pin finds the groove in the catching location 538. Upon release of the hammer shaft 531, this causes impaction of a locking mechanism into an anchor, thereby securing the anchor to an orthopedic device.

Figure 12A:
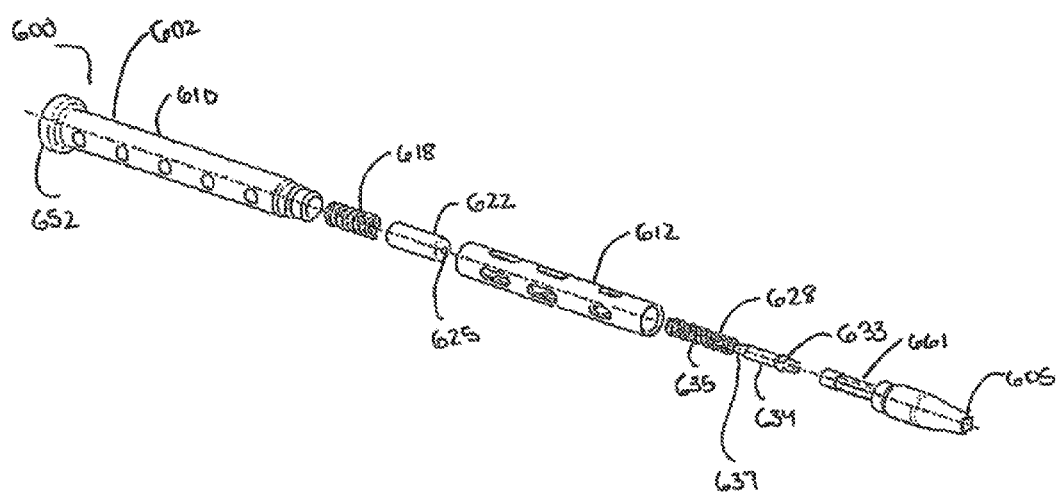
FIGS. 12A-12D illustrate different views of an alternative multi-functional insertion instrument according to some embodiments.
Figure 12B:
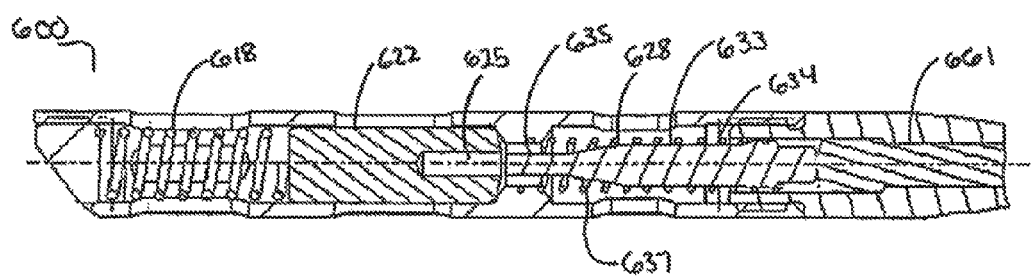
Figure 12C:
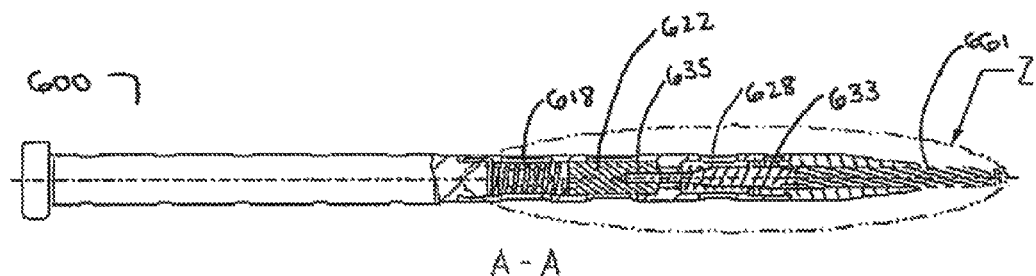
Figure 12D:
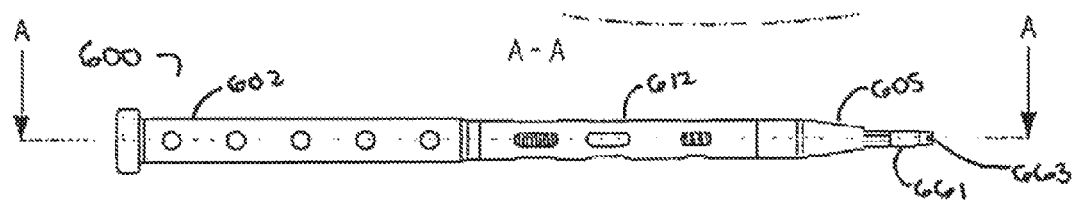

FIGS. 12A-12D illustrate different views of an alternative multi-functional insertion instrument according to some embodiments. The instrument 600 comprises a proximal portion 602 comprising a handle 610, a mid-sleeve 612 and a distal portion 605 that can be secured in series. These three components form a housing that encloses a firing spring 618 and firing cylinder 622 near the proximal portion 602 of the instrument, and a release spring 628 and swivel release 633 near the distal portion 605 of the instrument. The distal portion 605 of the instrument 600 also encloses a grasping element 661 having a distal tip 663 (as shown in FIG. 12D) for grasping the head of a locking mechanism.

The interaction of the swivel release 633 with the firing cylinder 622 helps form an impaction mechanism on the grasping element 661 that can force a locking mechanism into the head of an anchor. Unlike the previously described instruments, instrument 600 does not include a catch and release function. Rather, the instrument 600 relies on the alignment of the swivel release 633 to trigger an impaction mechanism to impact the locking mechanism into the head of the anchor, as discussed in more detail below.

The swivel release 633 comprises a body portion 634 that transitions into an extended narrower tip portion 635 via tapered sidewalls 637. The narrower tip portion 635 extends in the direction of the handle 610. During use, the swivel release 633 is retained at least in part within a release spring 635. In its natural state, the swivel release 633 is not aligned with a central longitudinal axis of the instrument 600. In this state, the narrower tip portion 635 of the swivel release will be crooked and oriented at an angle (e.g., misaligned) from the central longitudinal axis. This misalignment creates an interference that compresses the firing spring 618.

To create an impaction force, the narrower tip portion 635 of the swivel release 633 should be placed in alignment with the central hole 625 formed in the firing cylinder 622. In some embodiments, to align the narrower tip portion 635 of the swivel release 633 with the central hole 625, a user presses down on the instrument, such as on the back end 652 of the handle 610. As the user presses down, the release spring 635 compresses and stabilizes the swivel release 633 such that the swivel release 633 is aligned with the central longitudinal axis of the instrument. Once the swivel release 633 aligns with the central longitudinal axis, the narrower tip portion 635 of the swivel release will fall into a swivel release hole 625 formed in the firing cylinder 622, and will be impacted by the firing cylinder hole 625 bottoming out on the swivel release 633. The impaction force is created by the compressed firing spring 618, and helps to drive out the grasping element 661 through the distal end of the instrument 600. With the locking mechanism connected to the grasping element 661, the locking mechanism can be impacted and inserted into an anchor to thereby secure the anchor to an orthopedic device.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A surgical system comprising:
   a plate member having an aperture;
   an anchor insertable through the aperture of the plate member, the anchor having a plurality of arms;
   a locking mechanism insertable through the anchor, wherein downward insertion of the locking mechanism causes the plurality of arms to splay outwardly to thereby secure the anchor to the plate member; and
   an insertion instrument, wherein the insertion instrument is capable of both retaining the anchor and the locking mechanism, wherein the insertion instrument comprises a hammer shaft, a cocking sleeve, one or more cocking pins, a housing, and one or more catch pins that extend in one or more grooves formed in a wall of the housing,
   wherein axial movement of the cocking sleeve towards a proximal end of the insertion instrument causes the cocking pins to move the hammer shaft in a manner such that a chamfered surface of the hammer shaft splays the one or more catch pins to capture the hammer shaft.

2. The surgical system of claim 1, wherein the insertion instrument comprises a handle and a drive shaft that extends from the handle.

3. The surgical system of claim 2, wherein the drive shaft is configured to drive the anchor into bone.

4. The surgical system of claim 1, wherein the insertion instrument comprises a drive shaft for driving the anchor into bone and the hammer shaft is configured to deliver the locking mechanism into the anchor.

5. The surgical system of claim 4, wherein the hammer shaft is attached to the one or more cocking pins.

6. The surgical system of claim 5, wherein the hammer shaft is attached to the one or more catch pins.

7. The surgical system of claim 6, wherein the one or more catch pins are configured to catch the hammer shaft prior to delivering the locking mechanism into the anchor.

8. The surgical system of claim 7, wherein the insertion instrument further comprises a button that releases the hammer shaft from the catch pins, thereby delivering the locking mechanism into the anchor.

9. The surgical system of claim 4, wherein the hammer shaft comprises a spring-loaded device.

10. A surgical system comprising:
    a plate member having an aperture;
    an anchor having a head portion, wherein the anchor is insertable through the aperture of the plate member;
    a locking mechanism insertable through the head portion of the anchor, wherein downward insertion of the locking mechanism causes the head portion of the anchor to splay outwardly to thereby secure the anchor to the plate member; and
    an insertion instrument, wherein the insertion instrument is capable of both retaining the anchor and the locking mechanism, wherein the insertion instrument comprises a hammer shaft, a cocking sleeve, one or more cocking pins, a housing, and one or more catch pins that extend in one or more grooves formed in a wall of the housing,
    wherein axial movement of the cocking sleeve towards a proximal end of the insertion instrument causes the cocking pins to move the hammer shaft in a manner such that a chamfered surface of the hammer shaft splays the one or more catch pins to capture the hammer shaft.

11. The surgical system of claim 10, wherein the insertion instrument comprises a handle and a drive shaft that extends from the handle.

12. The surgical system of claim 11, wherein the drive shaft is configured to drive the anchor into bone.

13. The surgical system of claim 10, wherein the insertion instrument comprises a drive shaft for driving the anchor into bone and the hammer shaft is configured to deliver the locking mechanism into the anchor.

14. The surgical system of claim 13, wherein the hammer shaft is attached to the one or more cocking pins.

15. The surgical system of claim 14, wherein the hammer shaft is attached to the one or more catch pins.

16. The surgical system of claim 15, wherein the one or more catch pins are configured to catch the hammer shaft prior to delivering the locking mechanism into the anchor.

17. The surgical system of claim 16, wherein the insertion instrument further comprises a button that releases the hammer shaft from the catch pins, thereby delivering the locking mechanism into the anchor.

18. The surgical system of claim 13, wherein the hammer shaft comprises a spring-loaded device.

\* \* \* \* \*